United States Patent [19]

Farrington et al.

[11] Patent Number: 5,076,774

[45] Date of Patent: Dec. 31, 1991

[54] APPARATUS FOR FORMING THREE DIMENSIONAL COMPOSITE WEBS

[75] Inventors: Allan P. Farrington, Englishtown; Gerald M. Marshall, Somerville, both of N.J.

[73] Assignee: Chicopee, New Brunswick, N.J.

[21] Appl. No.: 312,017

[22] Filed: Feb. 16, 1989

[51] Int. Cl.$^5$ .............................................. D04H 1/00
[52] U.S. Cl. ...................................... 425/82.1; 19/301; 156/62.2; 425/83.1
[58] Field of Search ................. 19/300, 301, 148, 309, 19/306, 308; 425/80.1, 81.1, 82.1, 83.1; 156/62.2; 264/109, 121

[56] References Cited

U.S. PATENT DOCUMENTS

| | | | |
|---|---|---|---|
| 2,949,646 | 8/1960 | Clark | 425/80.1 |
| 2,993,239 | 7/1961 | Heritage | 425/81.1 |
| 3,056,173 | 10/1962 | Matter | 425/81.1 |
| 3,657,657 | 12/1973 | Teed | 19/301 |
| 3,717,905 | 2/1973 | Furbeck | 19/301 |
| 3,726,734 | 4/1973 | Lee | 19/301 |
| 3,744,091 | 7/1973 | Wood | 19/308 |
| 3,846,871 | 11/1974 | Kolbach | 19/301 |
| 3,963,392 | 6/1976 | Goyal | 425/81.1 |
| 3,973,291 | 8/1976 | Kolbach | 19/301 |
| 4,004,324 | 1/1977 | Bridge et al. | 425/82.1 |
| 4,032,274 | 6/1977 | Troy et al. | 264/121 |
| 4,054,628 | 10/1977 | Marshall | 19/301 |
| 4,388,056 | 6/1983 | Lee et al. | 425/83.1 |
| 4,701,294 | 10/1987 | Radwanski et al. | 264/121 |
| 4,741,941 | 5/1988 | Englebert et al. | 19/301 |
| 4,761,258 | 8/1988 | Enloe | 264/121 |
| 4,767,586 | 8/1988 | Radwanski et al. | 264/121 |

FOREIGN PATENT DOCUMENTS

| | | | |
|---|---|---|---|
| 3741082 | 7/1988 | Fed. Rep. of Germany | 19/301 |
| 2021169 | 11/1978 | United Kingdom | 19/144 |

Primary Examiner—Willard E. Hoag
Attorney, Agent, or Firm—Joseph F. Shirtz

[57] ABSTRACT

Apparatus for forming three dimensional shaped webs. The apparatus controls the flow of entraining air for an air laid web by restricting passage of the air through selected zones of a condensing surface. By limiting the open area in a zone of a suction plate the amount of fibers condensed over the zone is reduced permitting control of location of and amount of deposit. The duct work defining the conduit for the entraining air may also be shaped or provided with blocks to prevent scavenging of fibers which have already been deposited.

12 Claims, 5 Drawing Sheets

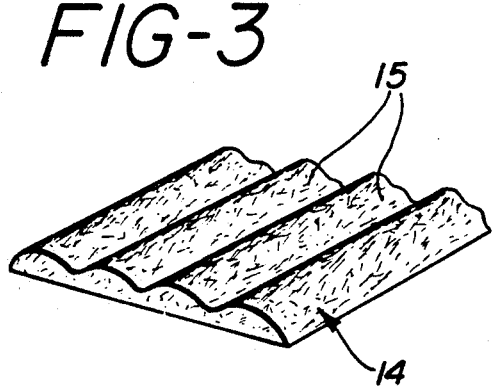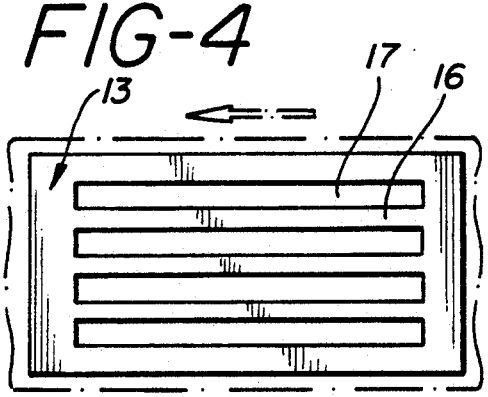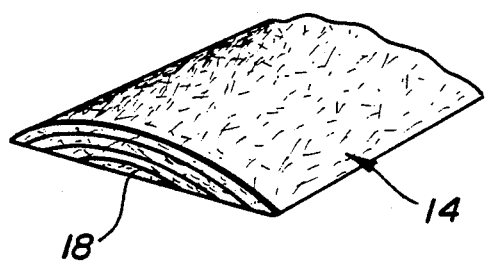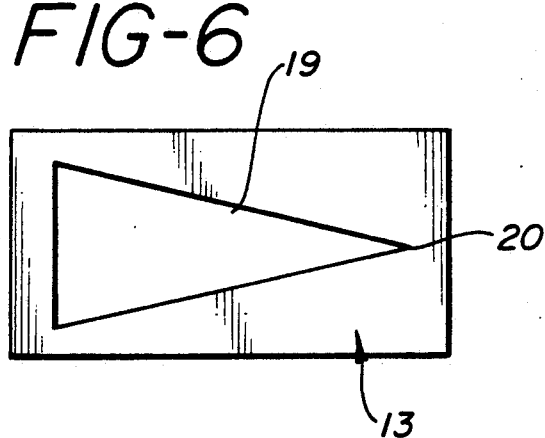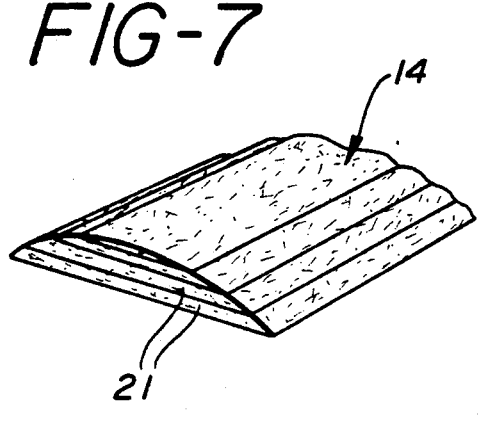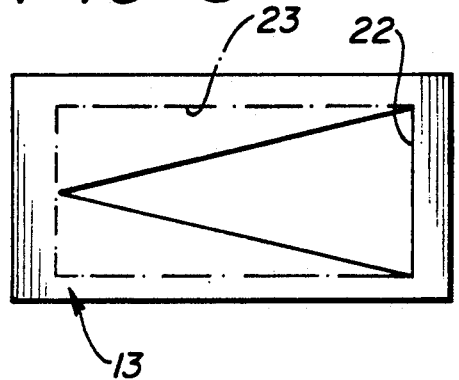

APPARATUS FOR FORMING THREE DIMENSIONAL COMPOSITE WEBS

TECHNICAL FIELD

The invention relates to formation of webs by condensing air entrained particles or fibers or both on a foraminous condensing screen and in particular, forming composite webs which vary in shape in directions transverse and perpendicular to the machine direction.

BACKGROUND OF THE INVENTION

Nonwoven fiber webs frequently consist of a random yet homogeneous agglomeration of long and short fibers. Long fibers are fibers of both natural and synthetic origin that are suitable for textiles. They are longer than 0.25 inches and generally range between 0.5 and 2.5 inches in length. Short fibers are suitable for paper-making and are generally less than about 0.25 inches long, such as woodpulp fibers or cotton linters. It is known in the art that strong nonwoven webs can be made by rapidly and reliably blending inexpensive short fibers with strong long fibers.

Nonwoven fabrics are less costly than woven or knitted material, yet are more or less comparable in physical properties, appearance, and weight. Thus, inexpensive nonwoven fabrics are available for a wide variety of products, including, hand towels, table napkins, sanitary napkins, hospital clothing, draperies, cosmetic pads, etc. These nonwoven webs can be particularly advantageous when formed as a layered or composite material having a varying area in horizontal cross-section at various vertical locations.

Methods and machines for making nonwoven fluff pulp pads and pre-shaped absorbent products are known, but do not provide for selective blending and layering of pulp, textile, and particulate materials. In particular, providing webs with a shaped profile and/or layered construction is a desirable yet unattained attribute of web forming apparatus.

For example, U.S. Pat. No. 4,701,294 discloses an apparatus for airforming of webs. The apparatus includes a striking mechanism which feeds fiberized material into a web forming zone. A gas delivery system forces a gas stream along the fiberizing mechanism and into the web forming zone. The gas-fiber stream induces a supplementary gas flow and a steering mechanism guides the induced flow to direct the fibers toward selected areas of a condensing surface. This apparatus is inefficient in its operation. After passing the vanes which make up the steering mechanism, the air flow tends to return to a more even flow thus reducing the effect of the steering vanes. Therefore, sharp, even transitions cannot be made without placing the vanes directly above the condensing surface, which in turn increases the resistance to air flow to the condensing surface and turbulence at the condensing surface. Furthermore, the apparatus is limited to the use of a single fiber input, thus not permitting a blend of entrained fibers of differing types.

SUMMARY OF THE INVENTION

In order to improve web structures and overcome the deficiency of prior methods and apparatus, the invention comprises modifying the air flow within the web forming zone of a nonwoven webber. An improved suction plate beneath a moving foraminous condensing belt is used to provide the modified air flow. For example, the plate may be provided with more free area or open area in one part as compared to another part of the suction plate.

As used herein, free area or open area refers to that portion of a given area which permits passage of air. For example, in a perforated plate, the free area or open area is the total area of perforation in a given area, that is the ratio of unoccluded area to total area and is often expressed as a percentage (i.e. 25% open area means ¼ of the total area is unoccluded).

The plate may have varying amounts of open area in different zones across the suction plate. The variation may range from 100% open down to a complete blockage. Thus, increased flow is provided through areas having the highest percentage open area and thereby causing an attendant increase in the amount of fiber condensed thereabove. By appropriate positioning of these zones, shaped structures may be formed which have sharp transitions. That is, shapes having step-like shape changes across the transverse width of the web.

The variation in percentage open area may be provided by masking portions of the suction plate. By masking the flow through the foraminous condensing screen, fiber deposition above the mask is virtually eliminated and fiber quantity condensing thereupon is negligible. Alternatively, masks may be provided above the screen and the masks may move with the screen.

BRIEF DESCRIPTION OF THE DRAWINGS

FIG. 3 is a perspective view of a web produced according to one embodiment of the present invention;

FIG. 4 is a top plan view of the suction plate for forming the product of FIG. 3;

FIG. 5 is a perspective view of a web produced according to a second embodiment of the invention;

FIG. 6 is a top plan view of the suction plate for forming the product of FIG. 5;

FIG. 7 is a perspective view of a web produced according to a third embodiment of the invention;

FIG. 8 is a top plan view of the suction plate for forming the product of FIG. 7;

DETAILED DESCRIPTION OF THE PREFERRED EMBODIMENTS

Figure 1:
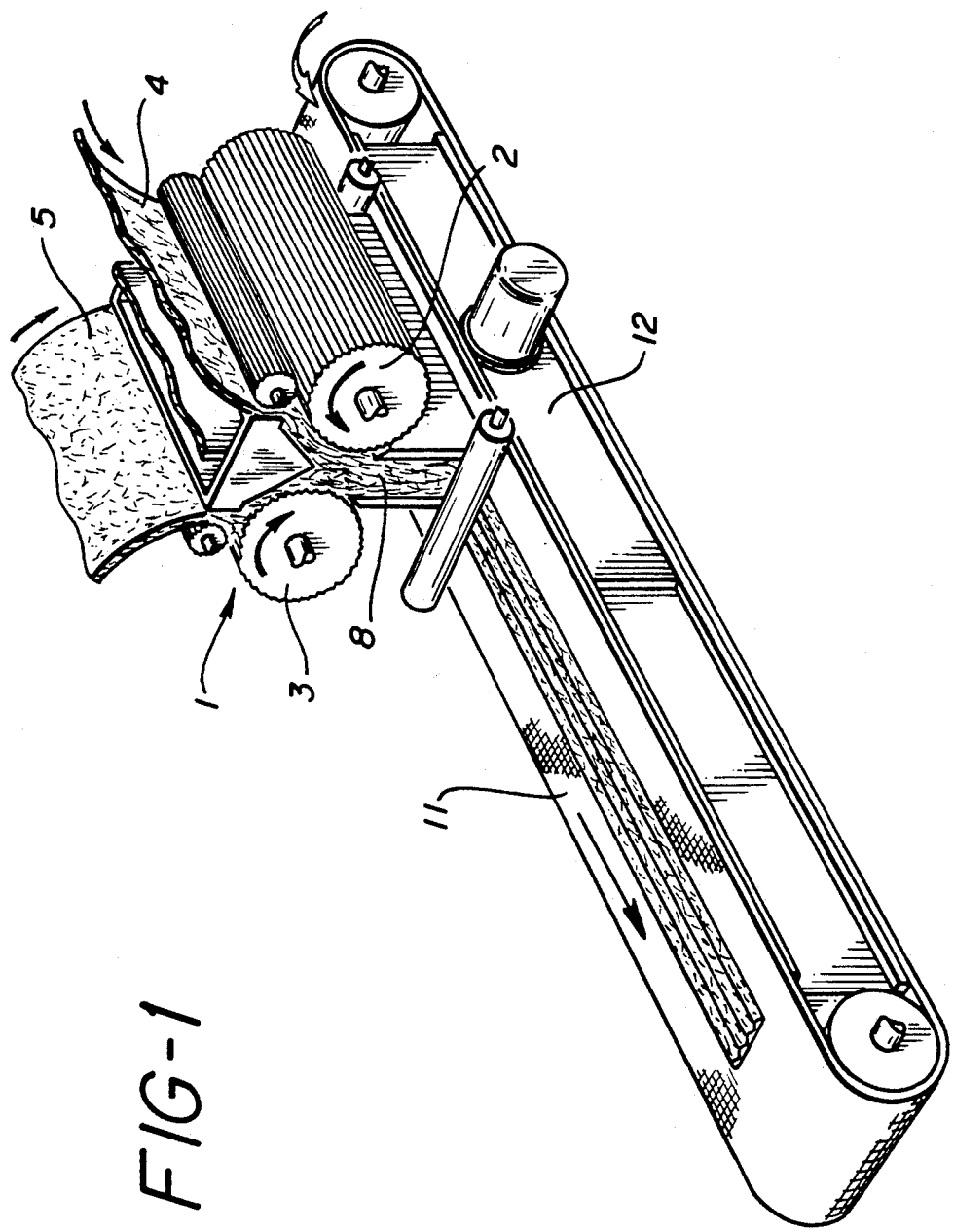
FIG. 1 is a perspective schematic view of a webber for use in the present invention.
Figure 2:
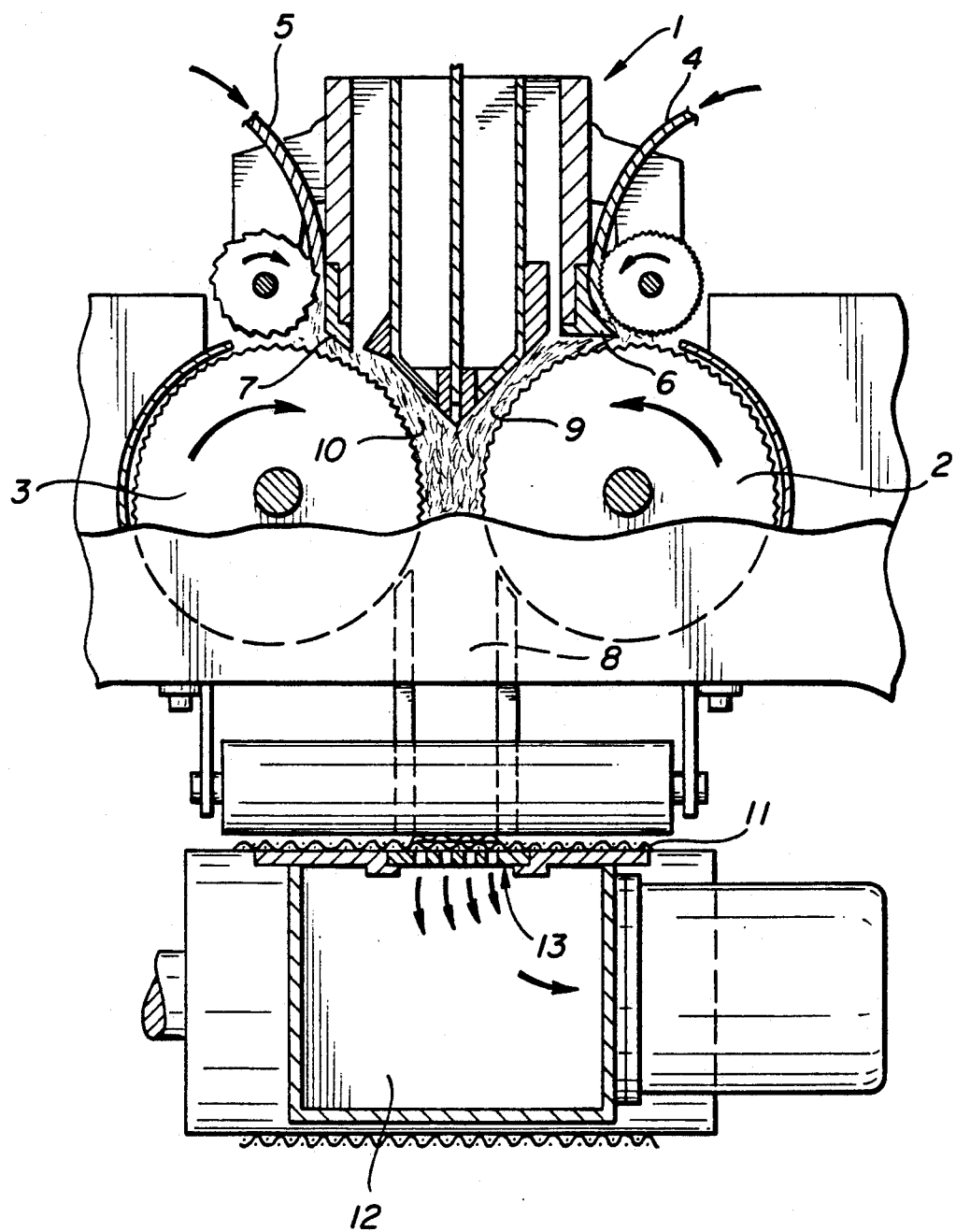
FIG. 2 is a schematic cross-section of the webber of FIG. 1.

Referring now to FIG. 1, there is shown a transverse webber 1 as shown in copending, commonly assigned U.S. application Ser. No. 99,875, filed Sept. 22, 1987 (ABT-19). The apparatus has a pair of fiber forming units such as lickerins 2,3. The lickerins 2,3 are fed fiber supplies 4,5 such as pulp board or the like. The fiber supplies 4,5 are fed past nose bars 6,7 and into contact with lickerins 2,3. The lickerins have a plurality of protrusions (not shown) which impact the supplies 4,5 to open and individualize the fibers thereof. The lickerins spin at speeds which optimize the opening and individualization of the particular fibers as known in the art. The supplies 4,5 are preferably of different fibers such that a blending occurs in duct 8.

The fibers exit the lickerins at openings 9,10 and are entrained in air moving through duct 8 until they condense on a foraminous surface formed by condensing screen 11.

The air flow through duct 8 is caused in part by a vacuum created in vacuum box 12. The vacuum is created in a known manner by, for example, a vacuum pump (not shown). This vacuum pulls air through the duct 8 and condensing screen 11 into the vacuum box 12. This air entrains fibers which flow with the air until obstructed by screen 11. The initial fibers impact the screen 11 and condense thereon. Subsequent fibers condense upon the initial fibers and entangle therewith building up a web of fibers having some degree structural integrity. Multiple feeds may be provided in order to produce a blended or multi-component structure.

Between condensing screen 11 and vacuum box 12 is a suction plate 13. The suction plate 13 supports the condensing screen 11 to prevent deflection of the screen in response to the forces of the vacuum and weight of the web formed by condensing of the fibers. The suction plate is perforated.

The amount of any particular fiber condensing at a particular location is dependent upon the amount of the particular fiber entrained in the air, the amount of air moving through the screen (condensing surface) and the speed that the screen moves in the machine direction.

In order to vary the amount of fiber condensed on the screen, in a direction transverse to the machine direction, the present invention provides suction plate 13 having varying opening sizes, number and shape in both the machine direction and transverse to the machine direction. Thus, the amount of air passing through the screen varies according to the variation in the openings of the suction plate.

Accordingly, a web 14 may be formed having ribs 15 (FIG. 3). The ribs extend parallel to each other and extend the length of the web 14 in the machine direction.

In order to form the ribbed structure of FIG. 3, a suction plate of the type shown in FIG. 4 is used. The suction plate has a number of small openings 16 which permit the passage of entraining air. The suction plate also defines a number of slots 17 which extend in the machine direction and parallel to one another. Slots 17 are, for example, 100% open to permit air passage to be free as compared to the non-passage of air through the solid remainder of the plate. In the area of slots 17 the only restriction to air passage is the condensing screen 11. Due to the lower resistance to air passage there will be an increased volume rate of flow of entraining air through the slots. As the fibers are entrained in the air in a substantially uniform amount, the increased volume rate of flow of air increases the amount of fibers condensed on the screen above the slots by selecting a separation between the slots which is smaller than the staple length of at least one of the fibers being deposited, some of the fibers will be deposited in a position crossing the separation and linking adjacent zones over the slots. Thus, the ribbed structure is formed having ribs formed by the increased fiber deposits over slots 17. As the ribs get thicker, they restrict flow a greater amount than the thin "valleys". Therefore, at a point defined by the size of the slots, the pressure differential across the screen 11 and the fiber type, the fibers begin to condense more uniformly.

A further embodiment of the product is shown in FIG. 5. A web 14 is formed having a rounded shape in transverse cross-section. This shape is built up from the center out by layering which forms a structure looking much like the rings of a tree trunk. Thus, a fiber or fiber blend may be entrained in air at the beginning of the condensing zone which will form a core 18. With different fibers entrained in different portions of the air in the machine direction causing a build up of layers. As will be seen, the arcuate layers shown in FIG. 5 would not have a sharp line of demarcation unless discrete supplies of entrained fibers are used.

The suction plate used to form web 14 of FIG. 5 is shown in FIG. 6. The suction plate 13 defines a zone 19 which is triangular in shape. If the suction plate is foraminous, the openings outside the zone 19 are masked. The apex 20 of the triangle is at the earliest point in the condensing zone, that is upstream along the machine direction. Thus, fibers will begin to condense only in the center of the screen over the apex. As the screen moves in the machine direction, the open portion tapers outward according to the shape of the triangle, and fibers begin to condense at the newly widened edge while fibers in the middle condense on top of the previously condensed fibers. In this embodiment, the geometry of the triangular zone determines the web shape. A long triangle which tapers slowly will create a web cross-section having a short radius of curvature. A shorter and more quickly tapering triangle creates a web having a gentler curve to its cross-section, that is, a longer radius of curvature. If desired, the ringed cross-section of the web may be created by placing baffles in duct 8 which extend transverse to the machine direction to separate the duct 8 into different zones. By feeding different fibers (type or color) into the different zones created by the baffles, a layered effect is created.

A strikingly different cross-sectional structure as shown in FIG. 7 may be obtained by simply rotating the suction plate of FIG. 6 180°. In this structure, the arcuate overall shape of the web is maintained, however, the internal structure differs. Rather than the rings of FIG. 5, the structure has the material laid down in flat layers 21. By placing the base 22 of the triangular zone at the initial point of the condensing zone, a broad base layer is laid down first. As the screen advances a narrower and narrower portion of the suction plate is open. Therefore, narrower layers are deposited creating the curved shape. Masked portions 23 need not be wholly occluded. Rather, the masked portions may just have a smaller amount of free area thus reducing the flow but not eliminating it. In this way the separation of the layers are less defined at their transitions. In fact, some open area across the entire web width may be necessary to prevent scavenging of already deposited fibers once the suction beneath the fibers is removed. It is preferred, however, to modify duct 8 so that the walls are positioned above the transition between the opened and closed portions of the plate. Thus, the already deposited portions are moved out of the suction zone as the open portion beneath them is removed thus preventing scavenging of the already deposited fibers. This result may also be obtained by blocking the duct 8 over the non-open portion of the plate.

Figure 9:
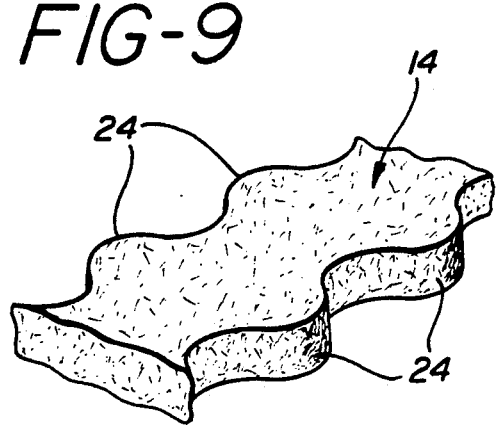
FIG. 9 is a perspective view of a product produced according to a fourth embodiment of the invention.

A further variation of the web is shown in FIG. 9. In this instance, an hourglass-like shape (for example) is provided. The web has bulges 24 along each longitudinal edge. The bulges 24 may be aligned on each edge, or may be offset to form a zig-zag form. The bulges 24 are depicted as recurring at equal distances and amplitudes, however, the pattern is determined by the masks of FIG. 10.

Figure 10:
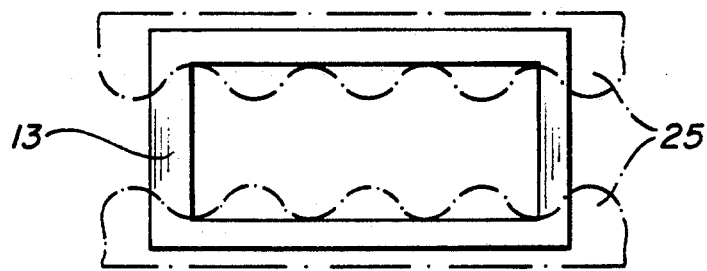
FIG. 10 is a top plan view of a suction plate for forming the product of FIG. 9.

In FIG. 10, a pair of variable width masks are shown. These masks are similar to those described above except they ride on top of and move with the condensing screen. A uniformly foraminous suction plate supports the condensing screen 11 and the moving masks 25 are synchronized for movement with the screen. Thus, the same portion of the screen 11 is masked during a given pass through the condensing zone. Because the portion is masked, only negligable amounts of fiber condense thereon and the web takes the shape of the unmasked portion. The moving masks 25 may take a number of shapes and are preferably continuous. Thus, the masks may be mounted to pass through the condensing zone out of the webber and around to the beginning. The shape of the mask may be non-repetitive along its length thus causing the web shape to repeat at a period determined only by the length of the continuous mask. The mask may be a flexible plastic or rubber strip, and may be made of a chain of metal links. The mask does not need to be as thick as the web created, rather it need only be thick enough to mask the suction plate and hold up under continuous use. However, a thicker mask will better define the product edge. In an extreme case, the moving masks along either edge of the screen are joined at points across the screen. In this manner, individual molded products are formed between the junctions without the need for thick and heavy molds. In such a case, the mask must recirculate in the same plane as the condensing screen.

Figure 11:
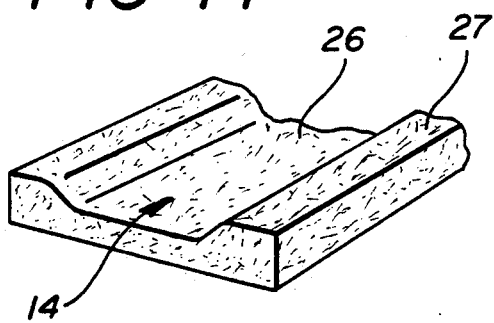
FIG. 11 is a perspective view of a product produced according to a fifth embodiment of the invention.
Figure 12:
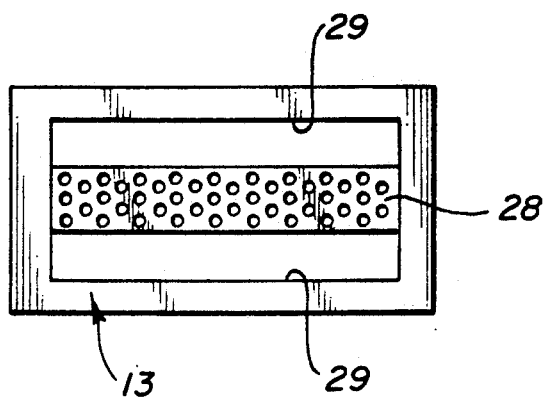
FIG. 12 is a top plan view of the suction plate for forming the product of FIG. 11.

A further modification may be made in keeping with the invention to provide a structure as shown in FIG. 11. There, the web is formed with a central longitudinal trough 26. The trough 26 is bounded by ridge 27 extending lengthwise along the edges of the web.

The structure of FIG. 11 is created by varying the open area across the width of the suction plate 13. Center 28 has fifty percent of the open area per unit area as compared with the marginal portions 29. That is, the ratio of open area to total area of center 28 is half the ratio of open area to total area of marginal portions 29. Thus, the volume rate of flow of entraining air per unit area is less in the center 28 than marginal portions 29. Therefore, a larger amount of fiber condenses along the edges forming ridges 27 which define trough 26.

Figure 13:
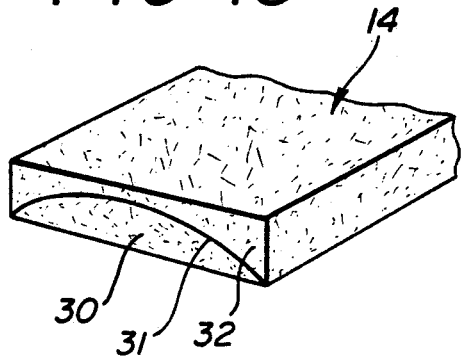
FIG. 13 is a perspective view of a product produced according to a sixth embodiment of the invention.

From combinations of the above-described embodiments compound structures may be formed. In FIG. 13 a composite structure is shown having a base layer 30 which has a part cylindrical outer surface 31. However, the external shape of the web is a common rectangle formed by cover layer 32. This is particularly advantageous when layers having different properties are desirable. The base layer may be an absorbent core with a hydrophobic cover layer 32.

Figure 14:
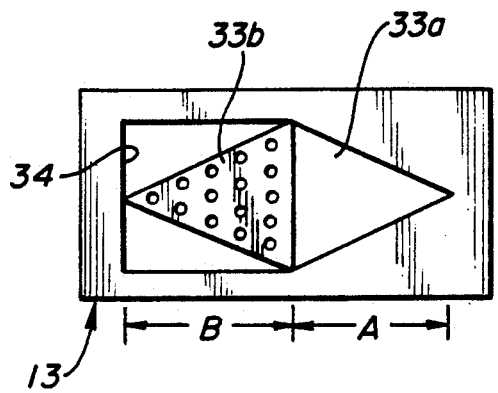
FIG. 14 is a top plan view of the suction plate for forming the product of FIG. 13.

The structure of FIG. 13 may be formed using the suction plate structure of FIG. 14. There the plate is divided which is the initial section passed over by the screen, the suction plate is masked except for triangle 33a. This creates the curved structure for the base layer as described above in connection with FIG. 6.

In section B, the triangle 33b is only partially opened, however, marginal triangles 34 are fully open. Thus, the cover layer 32 is formed by the increased flow along the edges and partial flow along the center. As the screen passes through section B, an increasing distance in from the edges is fully open thus increasing the width which has the highest rate of condensing. This is an inversion of section A thus providing a rectangle when sections A and B combine. Different fibers may be fed to form the base layer and cover layer It may be convenient to separate the duct between sections A and B when different fibers are fed, however, it is preferred to leave the duct unseparated in order to provide a blending of the fibers at the transition between A and B. Thus, a transition layer is formed to provide a more integral structure. In this way a composite product may be made for example having a cupped hydrophobic layer (section B) of fibers and an absorbent core (section A).

Figure 15:
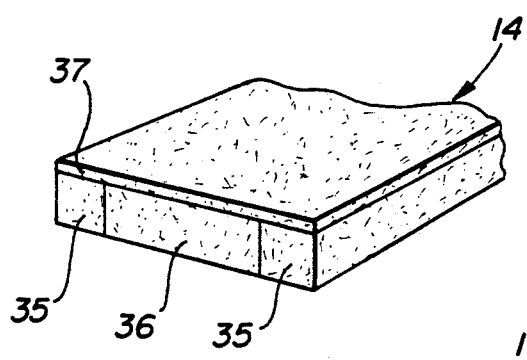
FIG. 15 is a perspective view of a product produced according to a seventh embodiment of the invention.

FIG. 15 shows a more complex composite structure which may be formed according to the present invention. The product has marginal wall 35 of a wicking or hydrophobic fiber, a central absorbent core 36 and a facing or backing layer 37. This structure forms an encased absorbent core for items such as sanitary napkins or diapers. The marginal walls 35 may be of a material which prevents lateral leakage of the fluid absorbed by absorbent core 36. The layer 37 can either be a wicking facing layer or a hydrophobic backing layer.

Figure 16:
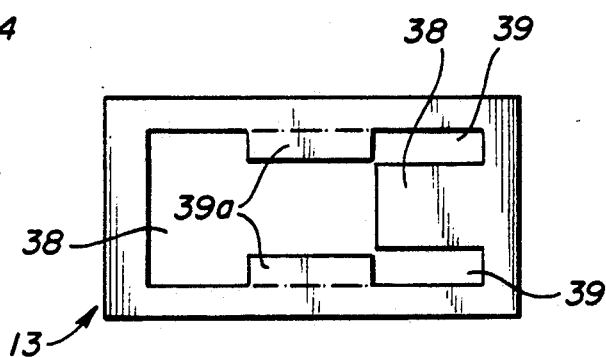
FIG. 16 is a top plan view of the suction plate for forming the product of FIG. 15.

The product of FIG. 15 may be formed by a suction plate modified as in FIG. 16. The plate is divided into three zones, the first zone forms marginal walls 35, the second zone forms absorbent core 36 and the third zone forms layer 37. In the first section, a rectangular central portion 38 is masked leaving two rectangular open section 39. As the foraminous screen passes over this portion, the marginal walls 35 of the product are formed. Because of the masking of central portion 38, little, if any, fiber condenses at the center of the screen. In the second section of the screen the absorbent core is formed. The suction plate is open over the entire length and breadth of this section. The duct 8 is narrowed, either by closer spacing of the walls or insertion of blocks, to a width approximately equal to that of section 38. Thus, the fibers condense over the narrowed center section. If an absorbent fiber such as wood pulp is fed into the webber at this portion, the absorbent fibers would condense over the central section thus forming absorbent core 36. In the final portion of the suction plate, the full width is open and the duct extends the full width of the plate. This causes the fibers to condense across the full width of the web. In this manner, layer 37 may be formed.

Figure 17:
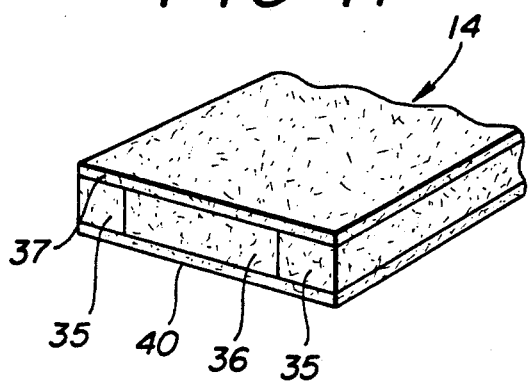
FIG. 17 is a perspective view of a product produced according to an eighth embodiment of the invention.

FIG. 17 depicts a further embodiment of the product where a top and bottom layer are both formed. The product has an absorbent core 36 and marginal walls 35 as described in the previous embodiment. However, this product has both a top layer 37 and a bottom layer 40.

Top layer 37 may, for example, be formed of fibers having desirable wicking qualities while bottom layer 40 is formed of hydrophobic fibers and, therefore, forms a barrier. Advantageously, bottom layer 40 may be formed of the same fibers as marginal walls 35.

Figure 18:
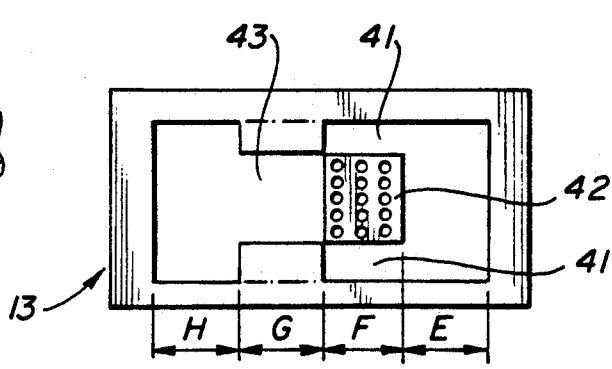
FIG. 18 is a top plan view of the suction plate for forming the product of FIG. 17.

To form the product of FIG. 17, a webber including the suction plate of FIG. 18 is used. The suction plate of FIG. 18 is similar to that of FIG. 16, however, it is divided into four portions; a first portion for the bottom layer, a second portion for the marginal walls, a third portion for the core and a fourth portion for the top layer.

In the first portion of the suction plate 13 of FIG. 18, the plate is open across the width of the desired web. Thus, the bottom layer 40 of the product is formed as the screen passes over the first portion of the suction plate. In the second portion F, the plate has rectangular full flow edge zones 41. The portion of the plate between the edge zones 41 is partial flow zone 42. Partial flow zone 42 has less open area per square inch than edge zones 41. Thus, fibers condense over edge zones 41 while the partial flow in partial flow zone 42 is sufficient to hold the already condensed fibers of layer 37 and thereby prevent the scavenging of fibers from the screen over partial flow zone 42 by the flow through edge zones 41.

In the third portion G of suction plate 13 of FIG. 18, the edges of the suction plate are substantially masked to lower air flow while center zone 43 is open, that is center zone 43 has open area. The duct is narrowed to prevent scavenging as described above in connection with the embodiment of FIG. 16. The fibers, therefore, condense in the web center forming the core. Partial flow to maintain marginal walls 35 may be provided but is not necessary. Walls 35 provide sufficient integrity themselves to prevent an appreciable amount of scavenging.

In the fourth portion H of FIG. 18, the full width of the suction plate has open area, thus the top layer condenses evenly across the width of the web. In this way, an outer cover layer or backing layer may be formed by condensing appropriate fibers in a thin top layer. The open area across the plate in portion H may have to vary to take into account the different resistance to flow of the air provided by walls 35 and core 36.

We claim:

1. In a web forming apparatus of the type having means to individualize fibers from a fiber supply, a condensing means spaced from said fiber supply for receiving fibers from said supply, means to discharge said fibers into a mixing means having a gas stream passing therethrough which entrains said fibers and conveys said fibers to said condensing means which permits passage of the gas stream while condensing said fibers thereupon to form a web, the improvement wherein:
(a) said condensing means is a moving foraminous surface which moves transverse to said gas stream; and
(b) a flow control means positioned adjacent to and opposite said mixing means to at least partially obstruct said foraminous surface to gas flow therethrough and defining a greater obstruction to passage of gas at a first position along said surface than at a second position in a direction of movement of said surface within said mixing means, said condensing means being moveable relative to said flow control means so said foraminous surface passes both said first position and said second position to cause a greater mass of fiber to be condensed at said second position than at said first position, said flow control means defining at least one polygonal aperture positioned for gas flow therethrough.

2. The improvement according to claim 1 wherein:
(a) said flow control means is a perforated suction plate positioned on the side of said foraminous surface opposite said mixing means.

3. The improvement according to claim 2 wherein:
(a) said suction plate defines a plurality of openings of substantially equal size to permit passage of said gas stream through said suction plate and said suction plate has a lesser number of said openings per unit area adjacent said first position than adjacent said second position.

4. The improvement according to claim 2 wherein:
(a) said suction plate defines a plurality of openings to permit passage of said gas stream through said suction plate and said suction plate defines openings adjacent said first position having lesser cross-sectional area per unit area of said suction plate than adjacent said second position.

5. The improvement according to claim 1 wherein:
(a) said flow control means is a stationary suction plate defining elongated open slots at said second position extending in the direction of movement of said foraminous surface.

6. The improvement according to claim 5 wherein:
(a) said suction plate occludes the foraminous surface at said first position.

7. The improvement according to claim 5 wherein:
(a) said suction plate is perforated to permit flow of gas therethrough at said first position.

8. The improvement according to claim 1 wherein:
an additional flow control means is moveable with said foraminous surface so the same part of said foraminous surface is continuously being masked as said foraminous surface passes across said gas stream.

9. The improvement according to claim 1 wherein:
(a) said mixing means is defined and enclosed by walls extending parallel to said gas stream; and
(b) at least one divider separates said mixing means into separate deposition zones and at least one of said deposition zones has a said first position and a said second position therein which are in a pattern different from a pattern of positions defined in a second deposition zone.

10. The improvement according to claim 9 wherein:
(a) said means to individualize fibers is adapted to supply at least a first individualized fibers to a first of said deposition zones and at least a second individualized fibers different from said first individualized fibers to a second deposition zone.

11. The improvement according to claim 1 further including:
a deposition means for depositing a layer of fibers onto at least a portion of said foraminous surface prior to entering said mixing means.

12. The improvement according to claim 1 wherein:
(a) said flow control means at least partially obstructs passage of said gas at more than two positions to restrict passage of said gas through each of said positions at a rate different than a rate passing through at least one other position.

* * * * *